United States Patent [19]

Polyakov et al.

[11] 4,299,816
[45] Nov. 10, 1981

[54] ACARICIDAL PREPARATION FOR DIAGNOSIS AND CONTROL OF ECTOPARASITES OF BEES

[76] Inventors: Anisim A. Polyakov, Proletarsky prospekt, 19, korpus 2, kv. 92; Vladimir S. Yarnykh, ulitsa Krasikova, 7, kv. 30, both of Moscow; Anatoly M. Smirnov, ulitsa Novaya, 5, kv. 86, Zheleznodorozhny Moskovskoi oblasti; Mark A. Simetsky, Teply Stan, 4 Mikroraion, korpus 45, kv. 136, Moscow; Evgeny A. Kudryavtsev, ulitsa Parkovaya, 3, kv. 30, Moskovskaya oblast, Balashikhinsky raion; German A. Talanov, Pulkovskaya ulitsa, 25, kv. 24; Alexandr A. Zakomyrdin, B. Rogozhsky pereulok, 10, korpus 1, kv. 127, both of Moscow; Boris N. Rudenko, OPKH "Milet", Zheleznodorozhny Moskovskoi oblasti; Pavel P. Rakhmanin, prospekt Mira, 18, korpus 2, kv. 100; Vyacheslav N. Guschin, ulitsa Kubinka, 10, kv. 31, both of Moscow, all of U.S.S.R.

[21] Appl. No.: 72,554

[22] Filed: Sep. 4, 1979

Related U.S. Application Data

[63] Continuation of Ser. No. 804,249, Jun. 7, 1977, abandoned.

[51] Int. Cl.$^3$ .................. A61L 9/04; A01N 47/10
[52] U.S. Cl. .................................. 424/45; 424/300
[58] Field of Search ..................... 424/45; 424/300

[56] References Cited

U.S. PATENT DOCUMENTS

| 2,321,023 | 6/1943 | Goodhue et al. | 424/45 |
| 3,258,326 | 6/1966 | Rabussier | 424/300 |
| 4,067,990 | 1/1978 | Dulat et al. | 424/300 |

OTHER PUBLICATIONS

Frear D. E. H., "Pesticide Index" 4th ed. pp. 88-8-9—College Science Publishers (1969).
Chem. Abst. 70 114157(g) (1969).

*Primary Examiner*—Douglas W. Robinson
*Attorney, Agent, or Firm*—Burton L. Lilling

[57] ABSTRACT

An acaricidal preparation for diagnosis and control of ectoparasites of bees is proposed including 0.006 to 0.167% by weight of an ester of N-methyl-carbamic acid, acetone being the balance, up to 100% by weight.

The acaricidal preparation may also include difluoro dichloromethane and have the following composition, in % by weight:

| ester of N-methyl-carbamic acid | 0.006 to 0.05 |
| acetone | 19.994 to 29.95 |
| difluoro dichloromethane | 80 to 70. |

The method of using the proposed acaricidal preparation is as follows: bee colonies are sprayed with the preparation in the form of aerosol at an ambient air temperature of 15° to 30° C., at a rate of 15 to 25 seconds per 50 cubic decimeters, once or up to four times, the interval between each treatment in the latter case being 12 to 24 hours.

The proposed acaricidal preparation is a highly effective agent for diagnosis and control of ectoparasites of bees. It ensures complete control of parasitic mites of genera *Varroa jacobsoni* and *Acarapis woodi* on bees, queens and drones without affectng them. The preparation is convenient in use, storage and transportation.

18 Claims, No Drawings

ACARICIDAL PREPARATION FOR DIAGNOSIS AND CONTROL OF ECTOPARASITES OF BEES

This is a continuation of application Ser. No. 804,249, filed June 7, 1977 and now abandoned.

The present invention relates to acaricidal preparations for diagnosis and control of ectoparasites of bees, in particular, acarine disease and varroatosis.

Acarine disease in an infestation of the respiratory organs of adult bees, caused by mites of genus *Acarapis woodi*.

Varroatosis is a disease caused by mites genus *Varroa jacobsoni*. Until recently, this disease was little known, while at present it is rapidly spreading, causing much harm.

Infestation by *V.jacobsoni* causes death of bee exhibit and birth of nonviable individuals. Affected bees exhibit deformities, such as absence of wings, amelia, deformity of thorax and abdomen. Apiaries lose drones, and the life of queens is shortened. The growth of bee colonies is affected. During the hibernation period bees are restless, and in the infested colonies the number of casualties is high.

Infested adult bees fly with difficulty, are restless, try to get rid of the mites, and die after long agony. More often than not, bees die beyond the apiaries. The signs of affliction manifest themselves gradually, and the productivity of the bee colonies remains sufficiently high during the first years. Two or three years later, the number of mites in the nest increase, and 20 to 30% of the bees are infested. The population of mites grows faster in weaker colonies; in stronger colonies, the brood is mostly infested on the outer frames of a beehive, however, in practice, even stronger families are sometimes highly infested.

It is known to use phenothiazine to control mites. Phenothiazine (thiodiphenylamine) is a complex organic compound of the heterocyclic series. By chemical structure it resembles methylene blue and thionine. Phenothiazine used for veterinary purposes is a tasteless greyish-green powder with a slight specific odor. It is insoluble in water and not wettable thereby; on the other hand, phenothiazine is soluble in acetone, benzene and ethers.

In apiaries affected by varroatosis, bee colonies are fumigated with the smoke of phenothiazine (1.5 g of the preparation in the course of three days). This treatment is repeated three times every seven to eight days. Bee colonies are thus treated in autumn in the absence of brood therein. Phenothiazine is used in the form of thermal pellets, fumigating strips or in combination with other agents thermally, producing aerosols. Such treatment does produce a certain effect, but, being an antihelminthic, phenothiazine does not control mites completely. Most mites remain alive (in the imago form), lay eggs, and their development continues. Moreover, each time bees are treated in this manner, about 200 to 300 of them die, including queens in most cases. As a result, complete bee colonies perish. In addition, phenothiazine of veterinary grade contains mechanical impurities. When aerosols are obtained thermally from phenothiazine pellets, the preparation decomposes yielding toxic products. The mechanical products of sublimation are harmful to bees.

It should also be pointed out that treatment with phenothiazine is complicated, in each case its quality must be checked, the required materials (oak or ash charcoal) are not always available, a professional fumigator has to be invited, and there is always the danger of the personnel being poisoned with the smoke of phenothiazine and beehives catching fire.

So far, no effective acaricidal preparations for diagnosis and control of varroatosis of bees are known.

It is, therefore, an object of the present invention to provide such a preparation.

According to the invention, an acaricidal preparation for diagnosis and control of ectoparasites of bees contains 0.006 to 0.167% by weight of an ester of N-methyl-carbamic acid, acetone constituting the balance, up to 100% by weight.

Esters of N-methyl-carbamic acid are known to be active isecti- and acaricides, and when methyl-N-methyl carbamate was used as a 0.5–1% aqueous emulsion and a wettable powder to control varroatosis by spraying bees, the bees died.

Thus, along with acaricidal action, methyl-N-methyl carbomate exhibits insecticidal properties. This is also true in the case of other aryl esters of N-methyl-carbamic acid.

Various organic solvents were tested, including rectified alcohol, isopropyl alcohol, chloroform, and benzene. None of these solvents proved to be useful. When beehives were treated without the effective agent, the above-mentioned solvents mixed with difluoro dichloromethane killed bees, while acetone taken in the same amount with difluoro dichloromethane did not harm them. At the same time, acetone is a good solvent for the above compounds, promotes formation of fine aerosol, and is fully compatible with difluoro dichloromethane.

For more convenient and effective use of the preparation, it should preferably be in the form of an aerosol and packed in special aerosol containers.

To this end a propellant is required, preferably difluoro dichloromethane, the preparation having the following composition, in % by weight:

| | |
|---|---:|
| ester of N-methyl-carbamic acid | 0.006 to 0.05 |
| acetone | 19.994 to 29.97 |
| difluoro dichloromethane | 80 to 70. |

Taken in the above amount, difluoro dichloromethane is not toxic at all for bees. In addition, it provides for a dense aerosol cloud.

Recommended for use as the esters of N-methyl-carbamic acid are, for example, methyl-N-methyl carbamate, 1-naphthyl-N-methyl carbamate, and ethyl-dimethyl-naphthyl-N-methyl carbamate.

As has been mentioned above, the preparation should preferably be used as an aerosol. To control mites of genera *Varroa jacobsoni* and *Acarapis woodi* infesting adult bees, queens and drones, the preparation should be used in spring and in summer, as well as in autumn, if necessary.

Bee colonies are sprayed with the preparation in the aerosol form at an ambient air temperature of 15° to 30° C., at a rate of 15 to 25 seconds per 50 cubic decimeters, once or up to four times, the interval between each treatment in the latter case being 12 to 24 hours.

In spring, bees are treated before breeding. When *V.jacobsoni* are detected in summer, to preserve bee colonies and maintain their productivity, summer treatments are recommended. They should be carried out preferably 30 days before honey gathering.

In autumn, before it freezes and before the bee colonies cluster, final treatment of all the infested bee colonies of the apiary should be carried out. Prior to mass treatment, all the available brood is removed from the bee colonies and exterminated.

Bee colonies should be sprayed in the evening when all the bees are back.

When bees are treated in beehives, the roof is removed first, then the heat-insulating blanket and the canvas. Then, an aerosol container or aerosol generator is taken, held at a distance of 10 to 15 cm from the frames, and the spray is directed into the space between the frames, right onto the bees. It takes from 1 to 1.5 seconds to spray each beeway. In the case of a multiplestory hive, the lower chamber is treated first, then each subsequent chamber in the order of their arrangement.

After the beeways have been sprayed, the broad nest is immediately recovered with the canvas, heat-insulating blanket, and the roof is replaced, whereafter the hive is sprayed again through the entrance for another 3 to 5 seconds, the entrance is narrowed to 1 cm and left in this state till morning.

The proposed preparation is most effective against V.jacobsoni.

Studies conducted to determine the efficiency of acaricidal treatment of bee colonies with the proposed preparation in summer indicate that in the presence of brood in a colony, four cycles of treatment are sufficient to kill 75 to 85% of all the mites, while similar treatment with phenothiazine exterminates only 30 to 40% of the mites.

Laboratory and field tests with the brood removed show that treatment with the proposed preparation in four cycles at 24-hour intervals gives an efficiency of 98 to 99.5% as compared to 50% when bees are treated with phenothiazine.

0.00806 g of the effective agent per cubic meter is the safe amount for bees.

The effective agent retains its activity over a long period of time and its residual acaricidal action on the surface of bees' bodies and hives remains unmitigated for 7 to 8 days, while phenothiazine has no residual acaricidal action at all. Owing to this feature of the proposed acaricide, bees are protected against infestation with mites for the above-mentioned period of time.

In addition, the preparation exhibits ovicidal properties with respect to the eggs laid by V.jacobsoni: after treatment of eggs, no larvae were hatched therefrom. Phenothiazine has no ovicidal action.

The procedure of controlling varroatosis with the proposed preparation also has certain advantages. Spraying aerosol from above into the beeways and through the entrance ensures treatment of all bees. Difluoro dichloromethane provides for a dense aerosol cloud penetrating into the beeways all the way to the bottom of the hive. At the same time, difluoro dichloromethane soon evaporates, and the effective agent dissolved in acetone remains suspended in the beehive for 20 to 30 minutes. Acetone evaporates completely after 30 minutes without precipitating on the bees and on the outer surface of the frames. The preparation remains suspended for a certain period of time ensuring better contact thereof with mites, bearing in mind that bees move incessantly on the surface of frames.

In addition, the use of the proposed preparation in acrosol form involves no thermal sublimation as in the case of phenothiazine, i.e. the detrimental effect of toxic substances is precluded.

In an aerosol container the preparation retains its acaricidal properties for a year.

Packed in aerosol containers, the preparation is convenient in use, storage and transportation. A single 320-ml container is enough to spray 10 to 12 beehives.

Thus, the use of the proposed preparation is aerosol form to control varroatosis of bees is most effective. Mites of genera *Varroa jacobsoni* and *Acarapis woodi* infesting bees, queens and drones are exterminated with no harm being done to the latter. The procedure of treating bee colonies permits easy and fast treatment of all beehives infested with the above mites.

A very important advantage of the proposed preparation is the possibility of using it in diagnosis of varroatosis of bees in apiaries, in spring, summer and autumn. For this purpose, a sheet of paper is placed on the bottom of a hive, and the bee colony is treated as usual. 30 minutes after the treatment, the paper sheet is withdrawn and if the colony is infested with V.jacobsoni, one can see mites on the sheet. Apart from the convenience of in-situ diagnosis, this method provides objective evidence as to the apiary being affected by varroatosis. Normally, 10 to 15 bee colonies out of 100 must be treated in this fashion.

Thus, the proposed method permits rapid and objective diagnosis of varroatosis of bees in situ.

The proposed preparation does not affect the quality of honey. Tests have been carried out to determine whether the effective agent leaves any residues in honey. To this end, samples in amounts of 50 g each were taken from different portions of frames in hives 24 hours after treatment. Hives were treated twice at a 24-hour interval. 10 g from each sample were checked for traces of the active ingredient by gas-liquid chromatography.

80 samples of honey from 40 beehives were checked in this manner. No traces of the acaricide were found.

Thus, the honey taken from beehives treated with the proposed preparation can be used in food without any restrictions.

The method of producing the acaricidal preparation is simple and includes the following steps.

A measured amount of an ester of N-methyl-carbamic acid is loaded into a vessel provided with an agitator, followed by acetone. The resulting mixture is agitated at room temperature for 15 minutes. Then, the end product is charged into aerosol generators or aerosol containers, on which a valve is mounted. In the latter case, the containers are filled with difluoro dichloromethane under pressure.

For a better understanding of the present invention, the following examples are given by way of illustration.

EXAMPLE 1

An acaricidal preparation of the following composition, in % by weight, is obtained:

| methyl-N-methyl carbamate | 0.01 |
|---|---|
| acetone | 99.9. |

When applied in aerosol form from an aerosol generator, the preparation exhibits pronounced acaricidal properties, exterminating 93 to 95% of mites without harming the bees.

EXAMPLE 2

An acaricidal preparation of the following composition, in % by weight, is obtained:

| | |
|---|---|
| 1-naphthyl-N-methyl carbamate | 0.02 |
| acetone | 99.98. |

When applied in aerosol form from an aerosol generator the preparation exhibits pronounced acaricidal properties, killing 94 to 96% of mites.

EXAMPLE 3

An acaricidal preparation of the following composition, in % by weight, is obtained:

| | |
|---|---|
| ethyl-dimethyl-naphthyl-N-methyl carbamate | 0.167 |
| acetone | 99.833. |

When applied in aerosol form from an aerosol generator, the preparation exhibits pronounced acaricidal activity, exterminating 95 to 98% of mites without harming the bees.

EXAMPLE 4

An acaricidal preparation of the following composition, in % by weight, is obtained:

| | |
|---|---|
| methyl-N-methyl carbamate | 0.025 |
| acetone | 19.975 |
| difluoro dichloromethane | 80. |

When applied with the above ratio of components, the preparation is highly effective, killing 98 to 99% of mites.

EXAMPLE 5

An acaricidal preparation of the following composition, in % by weight, is obtained:

| | |
|---|---|
| methyl-N-methyl carbamate | 0.01 |
| acetone | 29.99 |
| difluoro dichloromethane | 70. |

Doing no harm to the bees, this preparation kills only 70% of mites.

EXAMPLE 6

An acaricidal preparation of the following composition, in % by weight, is obtained:

| | |
|---|---|
| methyl-N-methyl carbamate | 0.03 |
| acetone | 29.97 |
| difluoro dichloromethane | 70. |

This preparation is highly effective, killing up to 100% of mites of genus *Varroa jacobsoni*, but it also kills a few bees: 30 to 50 per hive.

EXAMPLE 7

An acaricidal preparation of the following composition, in % by weight, is obtained:

| | |
|---|---|
| 1-naphthyl-N-methyl carbamate | 0.006 |
| acetone | 19.994 |
| difluoro dichloromethane | 80. |

The preparation is highly effective, killing up to 100% of mites of genus *Varroa jacobsoni* without harming the bees.

EXAMPLE 8

An acaricidal preparation of the following composition, in % by weight, is obtained:

| | |
|---|---|
| ethyl-dimethyl-naphthyl-N-methyl carbamate | 0.05 |
| acetone | 19.95 |
| difluoro dichloromethane | 80. |

The preparation exhibits high acaricidal properties, killing 95 to 98% of mites without harming the bees.

What is claimed is:

1. A method of controlling bee ectoparasite diseases selected from the group consisting of acarine and varroatosis comprising contacting bee colonies with a finely divided acaricidal composition comprising 0.006 to 0.167% by weight of an alkyl or naphthyl ester of N-methyl-carbamic acid, in acetone, at a temperature of 15°–30° C., at concentrations safe to bees and effective to control said ectoparasite diseases.

2. The method of claim 1, wherein the bee colonies are treated directly in a beeway of a beehive for 1 to 1.5 seconds, whereafter the beehive is enclosed and an additional amount of the preparation in aerosol form is introduced into the beehive through the entrance for 3 to 5 seconds.

3. The method of claim 1, wherein the acaricidal composition also includes difluorodichloromethane.

4. The method of claim 3, wherein bee colonies are treated directly in a beeway of a beehive for 1 to 1.5 seconds, whereafter the beehive is enclosed and an additional amount of the preparation in aerosol form is introduced into the beehive through the entrance for 3 to 5 seconds.

5. The method of claim 1, wherein the composition is in the form of an aerosol applied at a rate of 15 to 25 seconds per 50 cubic decimeters of beehive volume in one to four applications, repeated at intervals of 12 to 24 hours.

6. The method of claim 3, wherein the composition is in the form of an aerosol applied at a rate of 15 to 25 seconds per 50 cubic decimeters of beehive volume in one to four applications, repeated at intervals of 12 to 24 hours.

7. The method of claim 5, wherein the acaricidal composition is applied in concentrations of 0.00806 grams per cubic meter of beehive.

8. The method of claim 6, wherein the acaricidal composition is applied in concentrations of 0.00806 grams per cubic meter of beehive.

9. The method of claim 1, wherein acarine disease is caused by mites of genus *Acarapis woodi*, and varroatosis disease is caused by mites of genus *Varroa jacobsoni*.

10. An acaricidal composition for control of bee ectoparasite diseases selected from the group consisting of acarine and varroatosis comprising 0.006 to 0.167% by weight of an alkyl or naphthyl ester of N-methyl-carbamic acid, in acetone.

11. The acaricidal composition of claim 10, also including difluoro dichloromethane and having the following composition, in % by weight:

| | |
|---|---|
| ester of N-methyl-carbamic acid | 0.006 to 0.05 |
| acetone | 19.994 to 29.95 |
| difluoro dichloromethane | 80 to 70. |

12. The acaricidal composition of claim 10, wherein the ester of N-methyl-carbamic acid is methyl-N-methyl carbamate.

13. The acaricidal composition of claim 11, wherein the ester of N-methyl-carbamic acid is methyl-N-methyl carbamate.

14. The acaricidal composition of claim 10, wherein the ester of N-methyl-carbamic acid is 1-naphthyl-N-methyl carbamate.

15. The acaricidal composition of claim 11, wherein the ester of N-methyl-carbamic acid is 1-naphthyl-N-methyl carbamate.

16. The acaricidal composition of claim 10, wherein the ester of N-methyl-carbamic acid is ethyl-dimethyl-naphthyl-N-methyl carbamate.

17. The acaricidal composition of claim 11, wherein the ester of N-methyl-carbamic acid is ethyl-dimethyl-naphthyl-N-methyl carbamate.

18. The composition of claim 10, wherein acarine disease is caused by mites of genus *Acarapis woodi*, and varroatosis disease is caused by mites of genus *Varroa jacobsoni*.

* * * * *